United States Patent [19]

Klemm et al.

[11] Patent Number: 5,326,772

[45] Date of Patent: Jul. 5, 1994

[54] DIARYL COMPOUNDS FOR THEIR USE

[75] Inventors: Kurt Klemm, Allensbach; Wolf-Rüdiger Ulrich, Constance; Dieter Flockerzi, Allensbach, all of Fed. Rep. of Germany

[73] Assignee: Byk Gulden Lomberg Chemische Fabrik GmbH, Constance, Fed. Rep. of Germany

[21] Appl. No.: 881,319

[22] Filed: May 7, 1992

Related U.S. Application Data

[63] Continuation of Ser. No. 593,380, Sep. 28, 1990, abandoned, which is a continuation of Ser. No. 311,976, Feb. 17, 1989, abandoned, which is a continuation-in-part of Ser. No. 202,575, May 24, 1988, abandoned, which is a continuation-in-part of Ser. No. 31,834, Mar. 27, 1987, Pat. No. 4,975,440, which is a continuation-in-part of Ser. No. 781,808, Sep. 30, 1985, Pat. No. 4,707,486.

[30] Foreign Application Priority Data

Sep. 28, 1984 [CH] Switzerland ............... 04652/84-8
Sep. 28, 1984 [CH] Switzerland ............... 04653/84-0
Mar. 27, 1986 [CH] Switzerland ............... 01263/86-7
Feb. 19, 1988 [CH] Switzerland ............... 00629/88-0
Feb. 19, 1988 [CH] Switzerland ............... 00630/88-6

[51] Int. Cl.$^5$ .......................................... A61K 31/445
[52] U.S. Cl. ............................. 514/318; 546/194
[58] Field of Search ................................. 514/318

[56] References Cited

U.S. PATENT DOCUMENTS

| | | | |
|---|---|---|---|
| 4,380,547 | 4/1983 | Materne | 546/270 |
| 4,497,808 | 2/1985 | Zimmermann et al. | 546/187 |
| 4,558,058 | 12/1985 | Schönafinger et al. | 546/277 |
| 4,690,935 | 9/1987 | Taylor et al. | 514/356 |
| 4,707,486 | 11/1987 | Flockerzi et al. | 546/194 |
| 4,994,461 | 2/1991 | Ulrich | 514/252 |

OTHER PUBLICATIONS

Cancer Principles and Practice of Oncology, J. B. Lippincott Co. pp. 144–146 1985.
Merk Index 11th Edition pp. 1047–1048, 1989.
Schuller, Cancer Research, 50, 1645–1649, Mar. 1, 1990.
Gietzen, Med. Sci. Res., 18, 627–629, 1990.
Huebel, Supplement to Journal of Cancer Research and Clinical Oncology, 116, 446, A4.1'19.34, 1990.
Gietzen, Eur. J. Cancer, vol. 26, No. 8, 922–923, 1990.
FASEB Journal, No. 5, Part II, A1250, 5103, 1991.
Dorland's Illustrated Medical Dictionary, 24th Edition, p. 332, Saunders, 1965.
Tsuruo, "151 Atlas of Science: Pharmacology", pp. 325–327, 1987.
Panella et al., "A Phase . . . Solid Tumors", ASCO Abstract, 1989.
Wolf et al., "Application . . . Cell Lung Cancer", Sixth European Conference on Clinical Oncology and Cancer Nursing, Oct. 27–31, 1991.

Primary Examiner—Jane T. Fan
Attorney, Agent, or Firm—Jacobson, Price, Holman & Stern

[57] ABSTRACT

Optically pure diaryl compounds of formula I

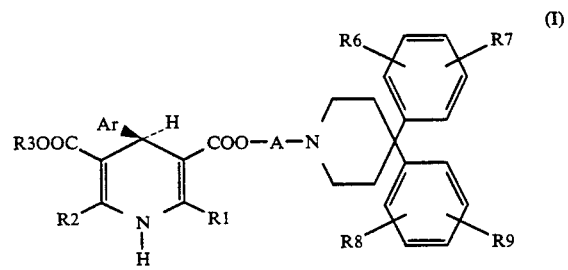

wherein the substituents and symbols have the meanings given int eh specification are proposed as active ingredients in medicaments for the treatment of tumors.

10 Claims, No Drawings

DIARYL COMPOUNDS FOR THEIR USE

This application is a continuation of Ser. No. 07/593,380 filed May 28, 1990, now abandoned which is a continuation of application Ser. No. 311,976 (now abandoned), filed Feb. 17, 1989, which is a continuation-in-part of application Ser. No. 202,575 (now abandoned), filed May 24, 1988, which is a continuation-in-part of application Ser. No. 031,834 (now U.S. Pat. No. 4,975,440), filed Mar. 27, 1987, which is a continuation-in-part of application Ser. No. 781,808 (now U.S. Pat. No. 4,707,486), filed Sep. 30, 1985.

FIELD OF INVENTION

The invention relates to optically pure diaryl compounds having an antineoplastic action, to their therapeutic use and to medicaments containing them. The compounds are employed in the pharmaceutical industry for the manufacture of medicaments.

TECHNICAL BACKGROUND

The use of calcium channel blocking compounds of the 1,4-dihydropyridine type for reducing metastasi s and neoplastic growth in mammals is described in U.S. Pat. No. 4,690,935. The antineoplastic action of the 1,4-dihydropyridines investigated (like Nimodipine and Nifedipine) is said to be attached to the calcium channel blocking activity of these compounds which permits them to be used in human medici ne for the treatment of vascular and cardi al disorders.—In U.S. Pat. No. 4,707,486 diaryl piperidine esters of 1,4-dihydropyridines and their use in cardiovascular diseases is disclosed.—In Application Ser. No. 031,834, filed Mar. 27, 1987, a certain enantiomer, (+)-3-methyl-5-[3-(4,4-diphenyl-1-piperidinyl) -propyl]-1,4-dihydro-2,6-dimethyl-4-(3-nitrophenyl) -pyridine-3,5-dicarboxylate, and its use for the treatment of cardiovascular diseases is claimed. The corresponding (−)-enantiomer, which has only an inferior antihypertensive activity, is mentioned in Ser. No. 031,834 only for comparative purposes.—In Application Ser. No. 272,775, filed Oct. 21, 1988, proceeding from PCT Application PCT/EP 87/00210, filed Apr. 17, 1987, 2-amino-1,4-dihydropyridines with a diaryl piperidine ester radical and their use in cardiovascular diseases is disclosed.

DESCRIPTION OF THE INVENTION

It has now been found, surprisingly, that the optically pure diaryl compounds of formula I

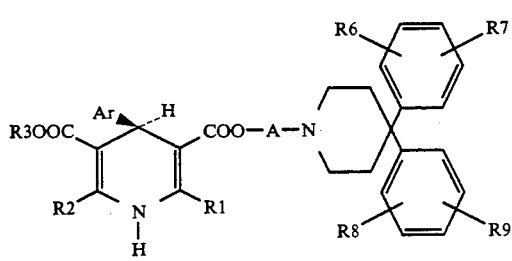

wherein
Ar represents a ring of the formula

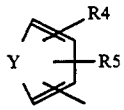

in which Y denotes oxygen (O), sulphur (S), vinylene (—CH═CH—), azomethine (—CH═N—) or a group of the formula

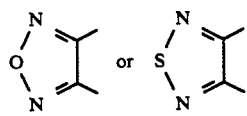

$R_1$ denotes hydrogen, 1-6C-alkyl or 3-7C-alkoxyalkyl, $R_2$ denotes hydrogen, amino ($NH_2$), 1-6C-alkyl or 3-7C-alkoxyalkyl, $R_3$ denotes hydrogen, 1-6C-alkyl or 3-7C-alkoxyalkyl, $R_4$ and $R_5$ are identical or different and denote hydrogen, hydroxyl, halogen, nitro, cyano, trifluoromethyl, 1-4C-alkyl, 1-4C-alkoxy, 1-4C-alkoxy which is completely or partly substituted by fluorine, 1-4C-alkoxycarbonyl, 2-5C-acyl, amino or mono- or di-1-4C-alkylamino, or together methylenedioxy, $R_6$, $R_7$, $R_8$ and $R_9$ are identical or different and denote hydrogen, hydroxyl, halogen, 1-4C-alkyl, 1-4C-alkoxy or 1-4C-alkoxy which is completely or partly substituted by fluorine, and A denotes 2-5C-alkyl ene or A1-0-A2, in which
A1 denotes 2-4C-alkylene and
A2 denotes 2-4C-alkylene or 2C-alkyleneoxy-2C-alkylene and their salts which have only inferior calcium channel blocking activity, have the ability to inhibit tumor cell growth in vitro which has a recognized relationship to in vivo activity in mammals.

Therefore, the present invention relates to a therapeutic method for reducing metastasis and neoplastic growth in a mammal which comprises administering a therapeutically-effective amount of a compound of formula I or a pharmaceutically-acceptable acid-addition salt thereof to a mammal in need of such therapy.

The cytostati cactivity of compounds I and their salts is coupled with an advantageous therapeutic range. Compounds I and their salts are useful as chemotherapeutic agents with few side effects for the treatment of tumors, in particular for the treatment of lung carcinomas, bronchial carcinomas, breast cancer, colon cancer and other malignant neoplasias. Accordingly, compounds I and their salts are useful for alleviation of pain and suffering in connection with cancer therapy, remission, alleviation of symptoms and extension of life expectancy.

The invention likewise relates to medicaments containing a compound of formula I or a pharmaceutically-acceptable acid-addition salt thereof.

The grouping of the substituents Ar and H in 4-position of the 1,4-dihydropyridine ring was accomplished on account of the publication of K. Tamazawa et al., J. Med. Chem. 29, 2504 (1986). Alternatively, compounds I can also be defined as optically pure compounds of formula Ia with uniform configuration

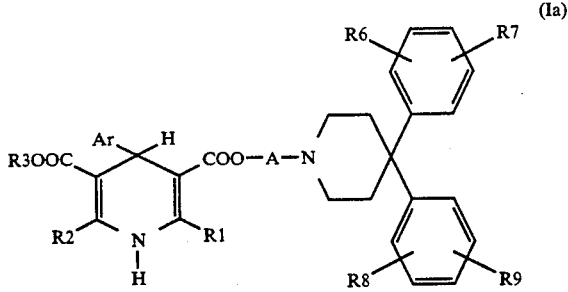

wherein Ar, R1, R2, R3, R4, R5, R6, R7, R8 and R9 and A have the meanings given above and which have the same configuration in the 4-position in the dihydropyridine as the diastereomer quinchonine (+)-1-ethoxymethyl-1,4-dihydro-5-methoxycarbonyl -2,6-dimethyl-4-(3-nitrophenyl) -pyridine-3-carboxylate, which is used as a starting compound and rotates linearly polarized light of wavelength 589 nm with $[\alpha]_D^{22} = +101.5°$ (c=1, chloroform).

1-6C-alkyl is straight-chain or branched and denotes, for example, a hexyl, neopentyl, isopentyl, butyl, i-butyl, sec.-butyl, t-butyl, propyl, isopropyl or, in particular, ethyl or methyl radical.

3-7C-alkoxyalkyl represents, for example, a methoxyethyl, ethoxyethyl, propoxyethyl, isopropoxyethyl, butoxyethyl, methoxypropyl, 2-methoxy-1-methylethyl or 2-ethoxy-1-methyl ethyl radical.

For the purposes of the invention, halogen denotes bromine and, in particular, fluorine and chlorine.

1-4C-alkyl is straight-chain or branched and denotes, for example, a butyl, i-butyl, sec.-butyl, t-butyl, propyl, isopropyl, ethyl or, in particular, methyl radical.

1-4C-alkoxy contains, in addition to the oxygen atom, one of the above-mentioned 1-4C-alkyl radicals. The methoxy radical is preferred.

1-4C-alkoxy which is completely or partially substituted by fluorine is, for example, 1,1,2,2-tetrafluoroethoxy, trifluoromethoxy, 2,2,2-trifluoroethoxy or difluoromethoxy.

1-4C-alkoxycarbonyl contains, in addition to the carbonyl group, one of the above-mentioned 1-4C-alkoxy radicals. The methoxycarbonyl radical and the ethoxycarbonyl radical are preferred.

2-5C-acyl contains, in addition to the carbonyl group, one of the above-mentioned 1-4C-alkyl radicals. The acetyl radical is preferred.

Mono- or di-1-4C-alkylamino contains, in addition to the nitrogen atom, one or two of the above-mentioned 1-4C-alkyl radicals. Di-1-4C-alkylamino is preferred, and in particular dimethyl-, diethyl- or diisopropylamino.

2-5C-alkylene is, for example, tetramethylene, 1,2-dimethylethylene, 1,1-dimethylethylene, 2,2-dimethylethylene, isopropylidene, 1-methylethylene, 2-ethylpropylene and, in particular, ethylene or propylene (trimethylene).

2-4C-alkylene represents ethylene (—CH$_2$—CH$_2$—), trimethylene (—CH$_2$—CH$_2$—CH$_2$—) and tetramethylene (—CH$_2$—CH$_2$—CH$_2$—CH$_2$—), ethylene being preferred.

2C-alkyleneoxy-2C-alkylene represents ethylene which is substituted by ethyleneoxy (—CH$_2$—CH$_2$—O—CH$_2$—CH$_2$—).

Suitable salts include all salts with acids, particularly the pharmacologically-acceptable salts of inorganic and organic acids customarily used in the pharmaceutical industry. Pharmacologically-unacceptable salts, which are, e.g., initially obtained as process products in preparing the compounds according to the invention on an i ndustri al scale, are readily converted into pharmacologically-acceptable salts by conventional processes known to those skilled in the art. Examples of suitable salts are water-soluble and water-insoluble acid-addition salts, such as the hydrochloride, hydrobromide, hydroiodide, phosphate, nitrate, sulfate, acetate, citrate, gluconate, benzoate, hibenzate, fendizoate, butyrate, sul fosal i cylate, maleate, 1 aurate, malate, fumarate, succinate, oxalate, tartrate, amsonate, metembonate, stearate, tosylate, 2-hydroxy-3-naphthoate, 3-hydroxy-2-naphthoate or mesylate.

The use, according to the invention, of compounds of formula I wherein Ar denotes phenyl, 2-nitrophenyl, 3-nitrophenyl, 2-cyanophenyl, 3-cyanophenyl, 2-(1,1,2,2-tetrafluoroethoxy) -phenyl, 3-(1,1,2,2-tetrafluoroethoxy) -phenyl, 2-difluoromethoxyphenyl, 3-difluoromethoxyphenyl, 2-chlorophenyl, 3-chlorophenyl, 2,3-dichlorophenyl, 2-fluorophenyl, 3-fluorophenyl, 2,3-methylenedioxyphenyl, 2-trifluoromethylphenyl, 3-trifluoromethylphenyl or 2,1,3-benzoxdiazol-4-yl, R1 denotes methyl, R2 denotes amino or methyl, R3 denotes methyl, ethyl or methoxyethyl, R6 denotes hydrogen, R7 denotes hydrogen or methoxy, R8 denotes hydrogen, R9 denotes hydrogen or methoxy, A denotes ethylene, propylene, butylene, 1,1-dimethylethylene, 2,2-dimethylethylene or AI-0-A2, A1 being ethylene and A2 being ethylene or ethyleneoxyethylene, and of their salts, has to be singl ed out.

The use, according to the invention, of compounds of formula I wherein Ar denotes 3-nitrophenyl, 2-chlorophenyl, 2,3-dichlorophenyl, 2-trifluoromethylphenyl, 2-difluoromethoxyphenyl, 2,3-methylenedioxyphenyl or 2,1,3-benzoxdiazol 4-yl, R1 denotes methyl, R2 denotes methyl, R3 denotes methyl, ethyl or methoxyethyl, R6, R7, R8 and R9 denote hydrogen and A denotes ethylene or propylene, and of their salts, has to be singled out particularly on one hand.

The use, according to the invention, of compounds of formula I wherein Ar denotes 3-nitrophenyl, 2-chlorophenyl, 2,3-dichlorophenyl, 2-trifluoromethylphenyl, 2-difluoromethoxyphenyl, 2,3-methylenedioxyphenyl or 2,1,3-benzoxdiazol-4-yl, R1 denotes methyl, R2 denotes amino, R3 denotes methyl, ethyl or methoxyethyl, R6, R7, R8 and R9 denote hydrogen and A denotes ethylene or propylene, and of their salts, has to be singled out particularly on the other hand.

The use, according to the invention, of compounds of formula I wherein Ar denotes 3-nitrophenyl, 2-chlorophenyl, 2,3-dichlorophenyl, 2-trifluoromethylphenyl, 2-difluoromethoxyphenyl, 2,3-methylenedioxyphenyl or 2,1,3-benzoxdiazol-4-yl, R1 denotes methyl, R2 denotes methyl, R3 denotes methyl, ethyl or methoxyethyl, R6, R7, R8 and R9 denote hydrogen and A denotes AI-0-A2, A1 being ethylene and A2 being ethylene or ethyleneoxyethylene, and of their salts, has to be singled out particularly in addition.

The use, according to the invention, of compounds of formula I wherein Ar denotes 3-nitrophenyl or 2,3-dichlorophenyl, R1 denotes methyl, R2 denotes methyl, R3 denotes methyl or ethyl, R6, R7, R8 and R9 denote hydrogen and A denotes ethylene or propylene, and of their salts, is preferred on one hand.

The use, according to the invention, of compounds of formula I wherein Ar denotes 3-nitrophenyl or 2,3-dichlorophenyl, R1 denotes methyl, R2 denotes amino, R3 denotes methyl or ethyl, R6, R7, R8 and R9 denote hydrogen and A denotes ethylene or propylene, and of their salts, is preferred on the other hand.

The use, according to the invention, of compounds of formula I wherein Ar denotes 3-nitrophenyl or 2,3-dichlorophenyl, R1 denotes methyl, R2 denotes methyl, R3 denotes methyl or ethyl, R6, R7, R8 and R9 denote hydrogen and A denotes A1-O-A2, A1 being ethylene and A2 being ethylene, and of their salts, is preferred in addition.

The use, according to the invention, of the following compounds has to be singled out by way of example:

(R) -3-methyl-5-[2-(4,4-diphenyl-1-piperidinyl) -ethyl[-1,4-dihydro-2,6-dimethyl -4-(3-nitrophenyl) -pyridine-3,5-dicarboxylate (R)-3 -methyl-5-[3-(4,4-diphenyl-1-piperidinyl) -propyl]-4-(3-cyanophenyl)-1,4-dihydro-2,6-dimethyl pyridine-3,5-dicarboxylate (R)-3-methyl-5-[2-(4,4-diphenyl-1-piperidinyl)-2-methyl -propyl]-1,4-dihydro-2,6-dimethyl-4-(3-nitrophenyl) -pyridine-3,5-dicarboxylate (R) -3-ethyl-5-[3-(4,4-diphenyl-1-piperidinyl) -propyl]-1,4-dihydro-2,6-dimethyl -4-(3-nitrophenyl) -pyridine-3,5-dicarboxylate (R)-3 -methyl-5-[3 -(4,4-diphenyl-1-pipe ridinyl)-p ro-pyl[-1,4-dihydro-2,6-dimethyl-4-[3-(1,1,2,2-tetrafluoroethoxi)-phenyl]-pyridine-3,5-dicarboxylate (R) -3-methyl-5-[2-(4,4-diphenyl-1-piperidinyl)-ethyl[-1,4-dihydro-2,6-dimethyl-4-[3-(1,1,2,2-tetrafluoroethoxy)-phenyl]-pyridine-3,5-dicarboxylate (S)-3-(2-methoxyethyl)-5-[2-(4,4-diphenyl-1-piperidinyl)-ethyl]-1,4-dihydro-2,6-dimethyl-4-(3-nitrophenyl)-pyridine-3,5-dicarboxylate (S)-3-(2-methoxyethyl)-5-[3-(4,4-diphenyl-1-piperidinyl)-propyl]-1,4-dihydro-2,6-dimethyl-4-(3-nitrophenyl)-pyridine-3,5-dicarboxylate (R)-3-methyl-5-{3-[4,4-di-(4-methoxyphenyl)-1-piperidinyl]-propyl}-1,4-2,6-dimethyl-4-(3-nitrophenyl)-pyridine-3,5-dicarboxylate (R)-3-methyl-5-[4-(4,4-diphenyl-1-piperidinyl)-butyl]-1,4-dihydro-2,6-dimethyl-4-(3 -nitrophenyl)-pyridine-3,5-dicarboxylate (R)-3-methyl-5-[1,1-dimethyl-2-(4,4-diphenyl-1-piperidinyl)-ethyl]-1,4-dihydro-2,6-dimethyl-4-(3-nitrophenyl)-pyridine-3,5-dicarboxylate (R)-3-ethyl-5-[3-(4,4-diphenyl-1-piperidinyl)-propyl]-1,4-dihydro-2,6-dimethyl-4-(2-difluoromethoxyphenyl)-pyridine-3,5-dicarboxylate (R)-3-ethyl-5-[3-(4,4-diphenyl-1-piperidinyl)-propyl[-1,4-dihydro-2,6-dimethyl-4-]3-(1,1,2,2-tetrafluoroethoxi)-phenyl]-pyridine-3,5-dicarboxylate (R)-3-ethyl-5-[3-(4,4-diphenyl-1-piperidinyl)-propyl]-1,4-dihyydro-2,6-4-(3-difluoromethoxyphenyl)-pyridine-3,5-dicarboxylate (R)-3 -methyl-5-[3 -(4,4-d i phenyl-1-piperidinyl)-propyl]-4-(2,3-dichlorophenyl)-1,4-dihydro-2,6-dimethyl pyridine-3,5-dicarboxylate (R)-3-methyl-5-[3-(4,4-diphenyl-1-piperidinyl)-propyl]-4-(2,1,3-benzoxdiazol-4-yl)-1,4-dihydro-2,6-dimethyl -pyridine-3,5-dicarboxylate (R)-3-methyl-5-[3-(4,4-diphenyl-1-piperidinyl)-propyl]-1,4-dihydro-2,6-dimethyl-4-(3-fluorophenyl)-pyridine-3,5-dicarboxylate (R)-3-methyl-5-[3-(4,4-diphenyl-1-piperidinyl)-propyl]-1,4-dihydro-2,6-dimethyl -4-(2-trifluoromethyl phenyl)-pyridine-3,5-dicarboxylate (R)-3-ethyl-5-[3-(4,4-diphenyl-1-piperidinyl)-propyl]-4-(2-cyanophenyl)-1,4-dihydro-2,6-dimethyl pyridine-3,5-dicarboxylate (R)-3 -methyl-5-[3-(4,4-diphenyl-1-piperidinyl)-propyl]-4-(2-chlorophenyl)-1,4-dihydro-2,6-dimethyl pyridine-3,5-dicarboxylate (R)-(−)-3-methyl-5-[3-(4,4-diphenyl-1-piperidinyl)-propyl]-1,4-dihydro-2,6dimethyl-4-(3-nitrophenyl)-pyridine-3,5-dicarboxylate (R)-3 -ethyl-5-[2-(4,4-diphenyl-1-piperidinyl)-ethyl]-2-amino-1,4-dihydro-6-methyl-4-(3-nitrophenyl)-pyridine-3,5-dicarboxylate (S)-3-(2-metho xyethyl)-5-[3-(4,4-diphenyl-1-piperidinyl)-propyl]-2-amino-1,4-dihydro-6-methyl-4-(3-nitrophenyl)-pyridine-3,5-dicarboxylate (R)-3 -methyl-5-[4-(4,4-diphenyl-1-piperidinyl)-butyl]-2-amino-1,4-dihydro-6-methyl-4-(3-nitrophenyl)-pyridine-3,5-dicarboxylate (R)-3-methyl-5-[2-(4,4-diphenyl-1-piperidinyl)-ethyl]-2-amino-1,4-dihydro-6-methyl-4-(2-nitrophenyl)-pyridine-3,5-dicarboxylate (R)-3-methyl-5-[2-(4,4-diphenyl-1-piperidinyl)-ethyl[-2-amino-1,4-dihydro-6ethyl-4-(3-nitrophenyl)-pyridine-3,5-dicarboxylate (R)-3-(propyl-2 )-5-[2-(4,4-diphenyl-1-piperidinyl)-ethyl]-2-amino-1,4-dihydro-6-methyl-4-(3-nitrophenyl)-pyridine-3,5-dicarboxylate (R)-3-hexyl-5-[2-(4,4-diphenyl-1-piperidinyl)-ethyl]-2-amino-1,4-dihydro-6-methyl-4-(3-nitrophenyl)-pyridine-3,5-dicarboxylate (S)-3-(2-n-butoxyethyl)-5-[2-(4,4-diphenyl-1-piperidinyl)-ethyl]-2-amino-1,4-dihydro-6-methy]-4-(3-nitrophenyl)-pyridine-3,5-dicarboxylate (R)-3-methyl-5-{2-[4,4-d i-(4-methoxyphenyl)-1-piperidinyl]-ethyl}-2-amino-1,4-dihydro-6-methyl-4-(3-nitrophenyl)-pyridine-3,5-dicarboxylate (R)-3-ethyl-5-[2-(4,4-diphenyl-1-piperidinyl)-ethyl]-2-amino-1,4-dihydro-6-methyl-4-(2-trifluoromethyl phenyl)-pyridine-3,5-dicarboxylate (R)-3-methyl-5-[2-(4,4-diphenyl-1-piperidinyl)-ethyl[-2-amino-1,4-dihydro-6-methyl-4-]3-(1,1,2,2-tetra fluoroethoxy)-phenyl[-pyridine-3,5-dicarboxylate (R)-3-ethyl-5-[2-(4,4-diphenyl-1-piperidinyl)- ethyl[-2-amino-1,4-dihydro-6-methyl-4-(2-difluoromethoxy-phenyl)-pyridine-3,5-dicarboxylate (R)-3-ethyl-5-[4-(4,4-diphenyl-1-piperidinyl)- butyl[-2-amino-1,4-dihydro-6-methyl-4-(2-difluoromethoxy-phenyl)-pyridine-3,5-dicarboxylate (R)-3-methyl-5-[2-(4,4-dihydroxyphenyl-1-piperidinyl)-ethyl]-2-amino-1,4-dihydro-6-methyl-4-(3-nitro-phenyl)-pyridine-3,5-dicarboxylate (R)-3-methyl-5-[2-(4,4-diphenyl-1-piperidinyl)-ethyl]-2-amino-4-(2,3-dichlorophenyl)-1,4- dihydro-6-methyl pyridine-3,5-dicarboxylate (R)-3-methyl-5-]2-(4,4-diphenyl-1-piperidinyl)-ethyl[-2-amino-4-(2,1,3-benzox-diazol-4-yl)-1,4-dihydro-6-methyl pyridine-3,5-dicarboxylate (R)-3-methyl-5-]2-(4,4-diphenyl-1-piperidinyl)-ethyl]-2-amino-4-(3-cyanophenyl)-1,4-dihydro-6-methylpyridine-3,5-dicarboxylate (R)-3-methyl-5-[2-(4,4-diphenyl-1-piperidinyl)-ethyl[-2-amino-1,4-dihydro-6-methyl-4-(2-methoxyphenyl)-pyridine-3,5-dicarboxylate (R)-3-methyl-5-[2-(4,4-diphenyl-1-piperidinyl)-ethyl[-2-amino-1,4-dihydro-6-methyl-4-(2-pyridyl)-pyridine-3,5-dicarboxylate (R)-3-methyl-5-[2-(4,4-diphenyl-1-piperidinyl)-ethyl]-2-amino-1,4-dihydro-6-methyl-4-(5-methyl-2-thi enyl)-pyridine-3,5-dicarboxylate (R)-3-methyl-5-{2-[4-(4-chlorophenyl)-4-phenyl-1-piperidinyl]-ethyl}-2-amino-1,4-dihydro-6-methyl-4-(3-nitro phenyl)-pyridine-3,5-dicarboxylate (R)-3-methyl-5-[3-(4,4-diphenyl-1-piperidinyl)-propyl[-2-amino-1,4-dihydro-6-methyl-4-(2-nitrophenyl)-pyridine-3,5-dicarboxylate (R)-3-methyl-5-[3-(4,4-diphenyl-1-piperidinyl)-propyl[-2-amino-1,4-dihydro-6-ethyl-4-(3-nitrophenyl)-pyridine-3,5-dicarboxylate (R)-3-(propyl-2)-5-[3-(4,4-diphenyl-1-piperidinyl)-propyl]-2-amino-1,4-dihydro-6-methyl-4-(3-nitrophenyl)-pyridine-3,5-dicarboxylate (R)-3 -hexyl-5-[3-(4,4-diphenyl-1-piperidinyl)-propyl]-2-amino-1,4-dihydro-6-methyl-4-(3-nitrophenyl)-pyridine-3,5-dicarboxylate (S)-3-(2-n-butoxyethyl)-5-[3-(4,4-diphenyl-1-piperidinyl)-propyl[-2-amino-1,4-dihydro-6-methyl-4-(3-nitrophenyl)-pyridine-3,5-dicarboxylate (R)-3-methyl-5-{3-[4,4-di(4-methoxyphenyl)-1-piperidinyl[-propyl}-2-amino-1,4-dihydro-6-methyl-4-(3-nitrophenyl)-pyridine-3,5-dicarboxylate (R)-3-ethyl-5-[3-(4,4-diphenyl-1-piperidinyl)-propyl[-2-amino-1,4-dihydro-6-methyl-4-(2-trifluoromethyl phenyl)-pyridine-3,5-dicarboxylate (R)-3-methyl-5-[3-(4,4-diphenyl-1-piperidinyl)-propyl[-2-amino-1,4-dihydro-6methyl-4-[3-(1,1,2,2-tetrafluoroethoxy)- phenyl[-pyridine-3,5-dicarboxylate (R)-3-ethyl-5-[3-(4,4-diphenyl-1-piperidinyl)-propyl]-2-amino-1,4-dihydro-6-methyl-4-(2-difluoromethoxyphenyl)-pyridine-3,5-dicarboxylate (R)-3-methyl-5-[3-(4,4-dihydroxyphenyl-1-piperidinyl)-propyl]-2-amino-1,4-dihydro-6-methyl-4-(3-nitrophenyl)-pyridine-3,5-dicarboxylate (R)-3-methyl-5-[3-(4,4-diphenyl-1-piperidinyl)-propyl]-2-amino-4-(2,3-dichlorophenyl)-1,4-dihydro-6-methylpyridine-3,5-dicarboxylate (R)-3-methyl-5-[3-(4,4-diphenyl-1-piperidinyl)-propyl]-2-amino-4-(2,1,3-benzoxazol-4-yl)-1,4-dihydro-6-methylpyridine-3,5-dicarboxylate (R)-3-methyl-S-[3-(4,4-diphenyl-1-piperidinyl)-propyl]-2-amino-4-(3-cyanophenyl)-1,4-dihydro-6-methylpyridine-3,5-dicarboxylate (R)-3-methyl-S-[3-(4,4-diphenyl-1-piperidinyl)-propyl[-2-amino-1,4-dihydro-6methyl-4-(2-methoxyphenyl)-pyridine-3,5-dicarboxylate (R)-3-methyl-5-[3-(4,4-diphenyl-1-piperidinyl)-propyl[-2-amino-1,4-dihydro-6methyl-4-(2-pyridyl)-pyridine-3,5-dicarboxylate (R)-3-ethyl-5-{2-[2-(4,4-diphenyl-1-piperidinyl)-ethoxy]-ethyl}-1,4-dihydro-2,6-dimethyl-4-(3-nitrophenyl)-pyridine-3,5-dicarboxylate (S)-3-(2-methoxyethyl)-5-{3-]3-(4,4-diphenyl-1-piperidinyl)-propoxi]-propyl}-1,4-dihydro-2,6-dimethyl-4-(3-nitrophenyl)-pyridine-3,5-dicarboxylate (R)-3-methyl-5-{2-[2-(4,4-diphenyl-1-pip eri dinyl)-ethoxi ]-ethyl}-1,4-dihydro-2,6-dimethyl-4-(2-nitrophenyl)-pyridine-3,5-dicarboxylate (R)-3-methyl-5-{2-[2-(4,4-diphenyl-1-pip eri dinyl)-ethoxi ]-ethyl}-1,4-dihydro-2,6-diethyl-4-(3-nitrophenyl)-pyridine-3,5-dicarboxylate (R)-3-(propyl-2)-5-{2-[2-(4,4-diphenyl-1-piperidinyl)-ethoxy]-ethyl}-1,4-dihydro-2,6-dimethyl-4-(3-nitrophenyl)-pyridine-3,5-dicarboxylate (R)-3-hexyl-5-{2-[2-(4,4-diphenyl-1-piperidinyl)-ethoxy]-ethyl}-1,4-dihydro-2,6-dimethyl-4-(3-nitrophenyl)-pyridine-3,5-dicarboxylate (R)-3-(2-n-butoxyethyl)-5-{2-[2-(4,4-diphenyl-1-piperidinyl)-ethoxy]-ethyl}1,4-dihydro-2,6-dimethyl-4-(3-nitrophenyl)-pyridine-3,5-dicarboxylate (R)-3-ethyl-5 -{2-[2-(4 4-diphenyl1-piperidinyl)-ethoxy]-ethyl}-1,4-dihydro-2,6-dimethyl-4-(2-trifluoromethyl phenyl)-pyridine-3,5-dicarboxylate (R)-3-methyl-5-{2-[2-(4,4-diphenyl-1-pip eri dinyl)-ethoxy]-ethyl}-1,4-dihydro-2,6-dimethyl-4-]3-(1,1,2,2-tetrafluoroet hoxy)-phenyl[-pyridine-3,5-dicarboxylate (R)-3-ethyl-5-{2-[2-(4,4-diphenyl-1-piperidinyl)-ethoxy]-ethyl}-1,4-dihydro-2,6-dimethyl-4-(2-difluoromethoxyphenyl)-pyridine-3,5-dicarboxylate (R)-3-methyl-5-{2-[2-(4,4-diphenyl-1-piperidinyl)-ethoxy]-ethyl}-1,4-dihydro-2,6-dimethyl-4-(3-nitrophenyl)-pyridine-3,5-dicarboxylate (R)-3-methyl-5-{2-[2-(4,4-diphenyl-1-piperidinyl)-ethoxy]-ethyl}-4-(2,3-dichlorophenyl)-1,4-dihydro-2,6-dimethylpyridine-3,5-dicarboxylate (R)-3 -methyl-5-{2-[2-(4,4-diphenyl-1-piperidinyl)-ethoxy]-ethyl}-4-(2,1,3-benzoxadiazol-4-yl)-1,4-dihydro-2,6-dimethylpyridine-3,5-dicarboxylate (R)-3-methyl-5-{2-[2-(4,4-diphenyl-1-p pe r dinyl)-ethoxy]-ethyl}-4-(3-cyanophenyl)-1,4-dihydro-2 6-dimethylpyridine-3,5-dicarboxylate (R)-3 -methyl-5-{2-[2-(4,4-diphenyl-1-piperidinyl)-ethoxy]-ethyl}-1,4-dihydro-2,6-dimethyl-4-(2-methoxyphenyl)-pyridine-3,5-dicarboxzylate (R)-3-methyl-5-{2-]2-(4,4-diphenyl-1-p perdinyl)-ethoxy]-ethyl}-1,4-dihydro-2,6-dimethyl-4-(2-pyridyl)-pyridine-3,5-dicarboxylate (R)-3-methyl-5-{2-[2-(4,4-diphenyl-1-p pemdinyl)-ethoxy]-ethyl}-1,4-dihydro-2,6-dimethyl-4-(5-methyl-2-thi enyl)-pyridine-3,5-dicarboxylate (R)-3-methyl-5-{3-[3-(4,4-diphenyl-1-piperdinyl)-propoxy]-propyl}-1,4-dihydro-2,6-dimethyl-4-(2-nitrophenyl)-pyridine-3,5-dicarboxylate (R)-3 -methyl-5-{3-[3-(4,4-diphenyl-1-piperdinyl)-propoxy]-propyl}-1,4dihydro-2,6-diethyl-4-(3-nitrophenyl)-pyridine-3,5-dicarboxylate (R)-3-(propyl-2 )-5-{3-[3-(4,4-diphenyl-1-piperidinyl)-propoxy]-propyl}-1,4-dihydro-2,6-dimethyl-4-(3-nitrophenyl)-pyridine-3,5-dicarboxylate (R)-3-hexyl-5-{3-[3-(4,4-diphenyl-1-piperidinyl)-propoxy]-propyl}-1,4-dihydro-2,6-dimethyl-4-(3-nitrophenyl)-pyridine-3,5-dicarboxylate (S)-3-(2-n-butoxyethyl)-5-{3-[3-(4,4-diphenyl-1-piperidinyl)-propoxy-propyl}-1,4-dihydro-2,6-dimethyl-4-(3-nitrophenyl)-pyridine-3,5-dicarboxylate (R)-3-ethyl-5-{3-[3-(4,4-diphenyl-1-piperidinyl)-propoxy]-propyl}-1,4-dihydro-2,6-dimethyl-4-(2-trifluoromethyl phenyl)-pyridine-3,5-dicarboxylate (R)-3-methyl-5-{3-[3-(4,4-diphenyl-1-piperidinyl)-propoxy]-propyl}-1,4-dihydro-2,6-dimethyl-4-]3-(1,1,2,2-tetrafluoroethoxy)-phenyl[-pyridine-3,5-dicarboxylate (R)-3-ethyl-5-{3-[3-(4,4-diphenyl-1-piperidinyl)-propoxy]-propyl}-1,4-dihydro-2,6-dimethyl-4-(2-difluoromethoxyphenyl)-pyridine-3,5-dicarboxylate (R)-3-methyl-5-{3-[3-(4,4-dihydroxyphenyl-1-piperidinyl)-propoxy]-propyl}-1,4-dihydro-2,6- dimethyl-4-(3-nitrophenyl)-pyridine-3,5-dicarboxylate (R)-3-methyl-5-{3-]3-(4,4-diphenyl-1-piperidinyl)-propoxy]-propyl}-1,4-dihydro-2,6-dimethyl-4-(3-nitrophenyl)-pyridine-3,5-dicarboxylate (R)-3-methyl-5-{3-[3-(4,4-diphenyl-1-piperidinyl)-propoxy]-propyl}-4-(2,3-dichlorophenyl)-1,4-dihydro-2,6-dimethylpyridine-3,5-dicarboxylate (R)-3-methyl-5-{3-]3-(4,4-diphenyl-1-piperidinyl)-propoxy]-propyl}-4-(2,1,3-benzoxdiazol-4-yl)-1,4-dihydro-2,6-dimethylpyridine-3,5-dicarboxylate (R)-3-methyl-5-{3-[3-(4,4-diphenyl-1-piperidyinyl)-propoxy]-propyl}-4-(3-cyanophenyl)-1,4-dyhydro-2,6-dimethylpyridine-3,5-dicarboxylate (R)-3-methyl-5-{3-[3-(4,4-diphenyl-1-piperidinyl)-propoxy]-propyl}-1,4-dihydro-2,6-dimethyl-4-(2-pyridyl)-pyridine-3,5-dicarboxylate and (R)-3-methyl-5-{3-[3-(4,4-diphenyl-1-piperidinyl)-propoxy]-propyl}-1,4-dihydro-2,6-dimethyl-4-(5-methyl-2-thienyl)-pyridine-3,5-dicarboxylate and of their salts.

The use, according to the invention, of the compound (R)-(+)-3-methyl-5-[3-(4,4-diphenyl-1-piperidinyl)-propyl]-1,4-dihydro-2,6-dimethyl-4-(3-nitrophenyl)-pyridine-3,5-dicarboxylate and of its salts is preferred particularly.

Particularly preferred subject matter of the invention is the use of those optically pure 1,4-dihydropyridines of formula I, which have—in particular as compared with their optical antipodes—only a minor influence on the cardiovascular system.

Furthermore the invention relates to the use of the compounds of formula I or pharmaceutically-acceptable acid-addition salts thereof for the manufacture of medicaments for reducing metastasis and neoplastic growth.

The synthesis of compounds of formula I is disclosed, for example, in European patent application 0 242 829. Compounds I can also be prepared by reacting optically pure dihydropyridines of formula II

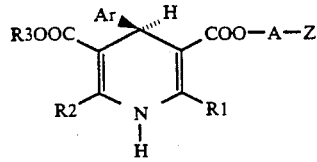

(II)

with diarylpiperidines of formula III

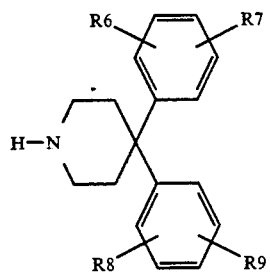

(III)

as such or in the form of their salts and, if desired, the salts obtained are then converted into the free bases or the bases obtained are then converted into the salts, Ar, R1, R2, R3, R6, R7, R8, R9 and A having the above-mentioned meanings and Z representing a suitable leaving group.

The reaction is carried out in suitable, preferably inert, organic solvent in the presence of water or without water. Examples of such solvents are ethers, such as dioxane, diethyl ether, tetrahydrofuran, glycol monoethyl ether or glycol dimethyl ether; ketones, such as acetone or ethyl methyl ketone; aromatic hydrocarbons, such as xylene or toluene; or chlorinated hydrocarbons, such as methylene chloride, chloroform, tetrachloroethylene or dichloroethane; or polar, aprotic solvents, such as dimethylformamide, n-methylpyrrolidone or dimethyl sul foxi de.

Depending on the reactivity of the educts, the reaction temperatures are optionally varied within a wide range. In general, the reaction is carried out at temperatures between 20° C. and 150° C., preferably between 20° C. and 100° C., in particular at the boiling point of the solvent used.

The process is conveniently carried out at atmospheric pressure or at increased pressure, work at atmospheric presssure being the rule.

Depending on the leaving group Z, which is for example a tosyl group or a trifluoromethanesulfonyl group, preferably a halogen atom, in particular a bromine atom, the reaction can, if desired, be carried out in the presence of a base (for example of an inorganic carbonate, such as potassium carbonate) or with the use of an excess of diarylpiperidine III.

The resultant compounds I are isolated and purified in a fashion which is known per se, for example by removing the solvent by distillation in vacuo and recrystallizing the resultant residue from a suitable solvent, or by subjecting it to one of the conventional purification methods, such as column chromatography on a suitable support material.

Acid-addition salts are obtained by dissolving the free base in a suitable solvent, for example in a chlorinated hydrocarbon, such as methylene chloride or chloroform, or in a low-molecular-weight aliphatic alcohol (ethanol or isopropanol), or in an open-chain or cyclic ether, such as dioxane or tetrahydrofuran, which contains the desired acid or to which the desired acid is subsequently added.

The salts are obtai ned by filtration, reprecipitation, precipitation with a nonsolvent for the addition salt, or by evaporation of the solvent.

The salts obtained are converted into the free bases by alkalization, for example using aqueous ammonia solution; and the free bases are, in turn, converted into acid-addition salts. In this fashion, pharmacologically-unacceptable acid-addition salts are easily converted into pharmacologically-acceptable acid-addition salts.

The starting compounds II are obtained from optically pure dihydropyridine carboxylic acids IV

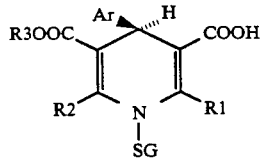

(IV)

by reaction with suitable bifunctional alkyl derivatives V $$Z-A-Z \qquad (V)$$

and subsequent removal of SG, Ar, R1, R2, R3 and A having the meanings given above, Z being a suitable leaving group and SG being a protecting group.

The reaction of IV with V is carried out preferably under basic conditions in the presence of a phase-transfer catalyst.

Illustrative catalysts, besides onium salts, such as tetrabutylammonium bromide or benzyltriethylammonium chloride, are particularly crown ethers, such as dibenzo-[18]crown-6, dicyclohexyl-[18]crown-6 and, in particular, [18]crown-6.

A suitable base is employed in at least a molar amount and preferably in excess thereof. The base is, e.g., an inorganic base, such as an alkali-metal hydroxide (for example sodium hydroxide or potassium hydroxide) or, in particular, an alkali-metal carbonate (for example sodium carbonate or, preferably, potassium carbonate). When the reaction is carried out in an anhydrous solvent, the hydroxide or carbonate used is preferably in finely-powdered form.

The reaction is carried out (depending on the type of phase-transfer catalyst, the leaving group Z and the base employed) in water-containing or anhydrous organic solvent, or in a mixture of water and a water-immiscible or sparingly water-miscible organic solvent. Examples of water/solvent mixtures include mixtures of water with chloroform, dichloromethane or benzene. Examples of water-containing or anhydrous solvents are dichloromethane, acetonitrile or acetone. The leaving group Z is preferably a halogen atom, in particular a bromine atom.

The choice of reaction temperature in the reaction of IV with V depends on the other reaction conditions; temperatures between 20° C. and the boiling point of the solvent employed are generally preferred.

Suitable protecting groups SG are, in particular, those groups which are introduced easily and in high yield into the precursor on which the compound IV is based, which do not undergo side reactions during the reaction of IV with V, and which are removed smoothly at the end of the reaction. Examples of preferred protecting groups SG are alkoxymethyl groups or benzyloxymethyl groups, in particular the ethoxymethyl group. The removal of the protecting group is carried out in acidic medium, for example in 1N hydrochloric acid or, preferably, in anhydrous formic acid, under reaction conditions which are known to the expert. The removal of the protecting group can also be carried out after the reaction with the diarylpiperidine III.

The solvents, bases and phase-transfer catalysts in the examples only represent an exemplaryselection. Which further combinations of solvents, bases and phase-transfer catalysts are also suitable is known to the expert on the basis of his expert knowledge.

The dihydropyridine carboxylic acids IV are known from Chem. Pharm. Bull. 28(9) 2809–2812 (1980), or are prepared in an analogous fashion to that described therein. The diaryl piperidines III are known from DE-OS 19 36 452. The bifunctional alkyl derivatives V are known or they can be prepared according to known processes.

The invention also relates to a process for the preparation of the compound (R)-(+)-3-methyl-5-[3-(4,4-diphenyl-1-piperidinyl)-propyl]-1,4-dihydro-2,6-dimethyl-4-(3-nitrophenyl)-pyridine-3,5-dicarboxylate (=compound I*) and its salts. The process is characterized by reacting an N-protected dihydropyridinecarboxylic acid of formula II*

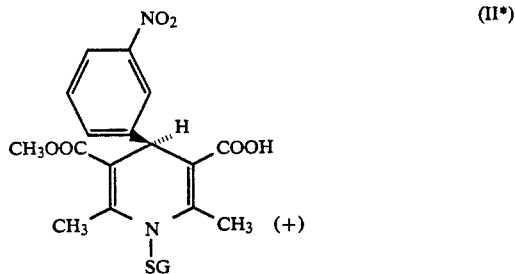

with 1,3-dibromopropane, and (after removal of the protecting group SG) reacting the resultant bromopropyl ester III*

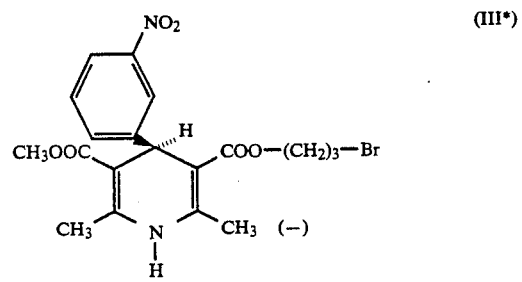

with diphenylpiperidine, or a salt thereof, to obtain the final product I*. Any produced salt of compound I* is optionally converted into the free base or a different salt; the free base is optionally converted into a salt. Such conversions are entirely conventional.

The reaction of II* with dibromopropane is carried out under basic conditions in the presence of a phase-transfer catalyst.

Illustrative catalysts, besides onium salts, such as tetrabutylammonium bromide or benzyltriethylammonium chloride, are particularly crown ethers, such as dibenzo-[18]crown-6, dicyclohexyl-[18]crown-6 and, in particular, [18]crown-6.

A suitable base is employed in at least a molar amount and preferably in excess thereof. The base is, e.g., an inorganic base, such as an alkali-metal hydroxide (for example sodium hydroxide or potassium hydroxide) or, in particular, an alkali-metal carbonate (for example sodium carbonate or, preferably, potassium carbonate). When the reaction is carried out in an anhydrous solvent, the hydroxide or carbonate used is preferably in finely-powdered form.

The reaction is carried out (depending on the type of phase-transfer catalyst and the base employed) in water-containing or anhydrous organic solvent, or in a mixture of water and a water-immiscible or sparingly water-miscible organic-solvent. Examples of water/solvent mixtures include mixtures of water with chloroform, dichloromethane or benzene. Examples of water-containing or anhydrous solvents are dichloromethane, acetonitrile or acetone.

The solvents, bases and phase-transfer catalysts in the examples only represent an exemplaryselection. Which further combinations of solvents, bases and phase-transfer catalysts are also suitable is known to the expert on the basis of his expert knowledge.

The choice of reaction temperature in the reaction of II* with dibromopropane depends on the other reaction conditions; temperatures between 20° C. and the boiling point of the solvent employed are generally preferred.

Suitable protecting groups SG are, in particular, those groups which are introduced easily and in high yield into the precursor on which the compound II* is based, which do not undergo side reactions during the reaction of II* with 1,3-dibromopropane, and which are removed smoothly at the end of the reaction. Examples of preferred protecting groups SG are alkoxymethyl groups or benzyloxymethyl groups, in particular the ethoxymethyl group. The removal of the protecting group is carried out in acidic medium, for example in 1N hydrochloric acid or, preferably, in anhydrous formic acid, under reaction conditions which are known to the expert.

The reaction of the bromopropyl ester III* with diphenylpiperidine is carried out in a fashion which is known to the expert for the reaction of alkyl halides withsecondary amines.

The reaction is carried out in suitable, preferably inert, organic solvent in the presence of water or without water. Examples of such solvents are ethers, such as dioxane, diethyl ether, tetrahydrofuran, glycol monoethyl ether or glycol dimethyl ether; ketones, such as acetone or ethyl methyl ketone; aromatic hydrocarbons, such as xylene or toluene; or chlorinated hydrocarbons, such as methylene chloride, chloroform, tetrachloroethylene or dichloroethane; or dipolar, aprotic solvents, such as dimethylsulfoxide or dimethylformamide.

Depending on the reactivity of the educts, the reaction temperatures are optionally varied within a wide range. In general, the reaction is carried out at temperatures between 20° C. and 150° C., preferably between 20° C. and 100° C., in particular at the boiling point of the solvent used.

The process is conveniently carried out at atmospheric pressure or at increased pressure, work at atmospheric presssure being the rule. The reaction is carried out in the presence of a base (for example an inorganic carbonate, such as potassium carbonate) or using an excess of diphenylpiperidine.

The resultant compound I* (according to the invention) is isolated and purified in a fashion which is known per se, for example by removing the solvent by distillation in vacuo and recrystallizing the resultant residue from a suitable solvent, or by subjecting it to one of the conventional purification methods, such as column chromotography on a suitable support material.

Acid-addition salts are obtained by dissolving the free base in a suitable solvent, for example in a chlorinated hydrocarbon, such as methylene chloride or chloroform, or in a low-molecular-weight aliphatic alcohol (ethanol or isopropanol), or in an open-chain or cyclic ether, such as dioxane or tetrahydrofuran, which contains the desired acid or to which the desired acid is subsequently added.

The salts are obtained by filtration, reprecipitating, precipitating with a nonsolvent for the addition salt, or by evaporation of the solvent.

The salts obtained are converted into the free bases by alkalization, for example using aqueous ammonia solution; and the free bases are, in turn, converted into acid-addition salts. In this fashion, pharmacologically-unacceptable acid-addition salts are easily converted into pharmacologically-acceptable acid-addition salts.

Compounds of formula II* are known from Chem. Pharm. Bull. 28(9) 2809–2811 (1980), or are prepared in an analogous fashion to that described therein.

A further process for the preparation of compound I* is characterized by reacting (±)-3-methyl-5-[3-(4,4-diphenyl-1-piperidinyl)-propyl]-1,4-dihydro-2,6-dimethyl-4-(3-nitrophenyl)-pyridine-3,5-dicarboxylate with a pure enantiomer of an optically-active acid. The resulting diastereoisomeric salts areseparated, and (+)-3-methyl-5-[3-(4,4-diphenyl-1-piperidinyl)-propyl[-1,4-dihydro-2,6-dimethyl-4-(3-nitrophenyl)-pyridine-3,5-dicarboxylate is liberated from the desired diastereoisomeric salt by adding a base. The thus-obtained free base is optionally converted into a salt.

Examples of useful optically-active acids are di-0,0'-p-toluoyltartaric acid or, in particular, L-(−)-di-0,0-benzoyltartaric acid. A suitableseparation process is preferably recrystallization.

The diastereoisomeric salts of uniform configuration which are separated by means of these methods are converted into the optically-active pure enantiomer of compound I*, preferably by adding inorganic base, such as ammonia, or by means of a basic ion exchanger.

The isolation and purification of compound I* is effected in a manner which is in itself known, for example by removing solvent by vacuum distillation and recrystallizing the resulting residue from a suitable solvent, or by subjecting it to a conventional method of purification, such as column chromotography over a suitable support.

Acid-addition salts are obtained by dissolving the free base in a suitable solvent, for example, in a chlorinated hydrocarbon, such as methylene chloride or chloroform, or a low-molecular aliphatic alcohol (ethanol or isopropanol), which contains the desired acid or to which the desired acid is subsequently added.

The salts are isolated by filtration, reprecipitation, precipitation with a non-solvent for the addition salt or by evaporating the solvent.

Resulting salts are converted into the free bases by rendering them alkaline, for example, with aqueous ammonia solution, and the free bases are, in turn, converted into acid-addition salts. Pharmacologically-unacceptable acid-additi on salts are converted in this manner into pharmacologically-acceptable acid-addition salts.

The preparation of the racemate on which compound I* is based, that is the preparation of the 1:1 mixture with the corresponding (+)-enantiomer, is described in U.S. Pat. No. 4,707,486.

The following preparation examples are intended to illustrate the invention in greater detail, without limiting it. M.p. denotes melting point, h represents hours, b.p. represents boiling point, and decomp. denotes decomposition, M represents molarity, N represents normality and d represents density.

EXAMPLES

End Products (−)-3-Methyl-5-[3-(4,4-diphenyl-1-piperidinyl)-propyl]-1,4-dihydro-2,6-dimethyl-4-(3-nitrophenyl)-pyridine-3,5-dicarboxylate hydrochloride A mixture of 86.6 g of (−)-3-methyl-5-(3-bromopropyl)-1,4-dihydro-2,6-dimethyl-4-(3-nitrophenyl)-pyridine-3,5-dicarboxylate, 50 g of 4,4-diphenylpiperidine hydrochloride and 69 g of finely powdered potassium carbonate is heated for 5 h in 300 ml of dimethyl formamide to 100° C. under a nitrogen atmosphere and with vigorous sti rring. After cooling, 500 ml of ethyl acetate and 1 l of water are added with vigorous stirring. The phases are separated; the organic phase is washed four times with water, dried over sodium sulfate and concentrated in vacuo. The residue is dissolved in 1 l of dioxane; then 15.2 ml of concentrated hydrochloric acid solution (12.5 M, d =1.19) are added, and about 200 ml of the solvent mixture are removed by distillation in vacuo. The product crystallizes spontaneously on standing at room temperature or after inoculation or trituration, and is filtered off by suction after 16 h, washed with dioxane and diisopropyl ether, and dried at 80 to 100° C. in vacuo. For further purification the crude product is dissolved in dichloromethane. After addition of 800 ml of dioxane the dichlormethane is distilled off. The product which crystallizes after inoculation on standing at room temperature for 16 h is filtered off by suction, washed with dioxane and diisopropyl ether, and dried at 100° C. in vacuo. 97 g of the title compound {m.p. 158° C. to 160° C. and $[\alpha]_{436}^{22} = -39°$ (c=1, methanol) or $[\alpha]$=-14,4 (c =1, methanol)} are obtained.

Alternatively, the title compound is obtained as follows:

64.6 g of (±)-3-methyl-5-[3-(4,4-diphenyl-1-piperidinyl)-propyl]-1,4-dihydro-2,6-dimethyl-4-(3-nitrophenyl)-pyridine-3,5-dicarboxylate hydrochloride are dissolved in 300 ml of dichloromethane. The solution is washed once with 100 ml of concentrated aqueous ammonia solution and twice with 100 ml of water. The organic phase is dried over sodium sulfate and concentrated. The obtained residue (60.91 g) and 37.63 g of L-(−)-di-0,0'-benzoyltartaric acid hydrate {having a specific rotation $[\alpha]_c^{22}$ or −108.1° (c=1, methanol)} are together dissolved in 400 ml of ethanol at the boi l. Allowing the stirred solution to cool slowly gives a first crop of crystals (55 g of di-0,0'-benzoyltartrate of the title compound; slightly yellowish crystals) which is dissolved again at the boil in a mixture of chloroform and methanol (4+1). When the crystals have just dissolved, ethyl acetate (20 per cent by volume of the mixture of chloroform/methanol) is added to the boiling solution, and the mixture is allowed to cool slowly with stirring. The obtainedsecond crop of crystals (50 g) is recrystallized three times in the same way. A third (36 g with $[\alpha]_D^{22} = -47.5°$), fourth (33 g with $[\alpha]_D^{22} = -49.4°$) and fifth {31 g with $[\alpha]_D^{22} = -50.4°$ (c=1, methanol)} crop of crystals is obtained successively. The fifth crop of crystals is dissolved in 500 ml of dichloromethane. The solution is washed twice with 150 ml of concentrated aqueous ammonia solution in each case and three times with 100 ml of water in each case. The organic phase is concentrated, and the residue is worked up as described above. Yield: 19.8 g, $[\alpha]_D^{22} = -14.3°$ (c=1, methanol).

2. (+)-3-Ethyl-5-]3-(4,4-diphenyl-1 -piperidinyl)-propyl[-2-amino-1,4-dihydro-6-methyl-4-(3-nitrophenyl)-pyridine-3,5-dicarboxylate 60 g of (±)-3-Ethyl-5-[3-(4,4-diphenyl-1-piperidinyl)-propyl]-2-amino-1,4-dihydro-6-methyl-4-(4-nitrophenyl)-pyridine-3,5-dicarboxylate and 36,2 g of L-(−)-di0,0'-benzoyltartaric acid hydrate {in this example having a specific rotation $[\alpha]_D^{22} = -108.4°$ (c=1, methanol)} are together dissolved in methanol/dichloromethane (9+1). After concentration of the solution, the solid foamed residue is taken up at the boil in 300 ml of a mixture of methyl ethyl ketone and methanol (2+1), and the well-stirred clear solution is then allowed to cool slowly. A first crop of crystals {33 g, m.p. 165°-166° C., $[\alpha]_D^{22} = -17.8$ (c=1 methanol)} is obtained which yields after renewed recrystallization from methyl ethyl ketone/methanol (2+1) a second crops of crystals {22 g, $[\alpha]_D^{22} = -10.8°$ (c=1 methanol)}. The coarse yellowish needles are dissolved in 400 ml of dichloromethane. The solution is extracted wi th 300 ml of concentrated aqueous ammonia solution and subsequently three times with 100 ml of water in each case. The organic phase is dried over sodium sulfate and concentrated. The obtained solid foamed residue (14.3 g) is dissolved together with 2.6 g of fumaric acid in methanol, and the solution is concentrated again. The residue is dissolved in a boiling mixture of ethyl acetate and 2-propanol (9+1). The solution is allowed to cool slowly, and 12.4 g of the title compound are obtained as fine needles of m.p. 151°-152° C. and $[\alpha]_D^{22} = -42.0°$ (c=1, methanol).

The freee base of the title compound obtained after the extraction with ammonia can be precipitated in petroleum ether in amorphous form. A fine yellowish powder of m.p. 96°-104° C. (slow deliquescence) and $[\alpha]_D^{22} = +57.6°$ (c=1, methanol) is obtained.

(+)-3-Methyl-5-{2-[2-(4,4-diphenyl-1-piperidinyl-ethoxy]-ethyl}-1,4-dihydro-2,6-dimethyl-4-(3-nitrophenyl)-pyridine-3,5-dicarboxylate hydrochloride 3 ml of oxalyl chloride are added to 997 mg of (+)-3-methyl-1,4-dihydro-2,6-dimethyl-4-(3-nitrophenyl)-pyridine-3,5-dicarboxylate. The mixture is stirred at room temperature until no further evolution of gas can be detected. The batch is concentrated to dryness three times with the addition of 5 ml of absolute toluene each time. The resulting brown solid residue is suspended in 3 ml of absolute methylene chloride and the suspension is added dropwise to a solution, cooled to 0° C., of 1.09 g of N-[2-(2-hydroxyethoxy)-ethyl[-4,4-diphenylpiperidine and 0.6 ml of triethylamine, while gassing with $N_2$. After the dropwise addition, the mixture is stirred at room temperature for a further 2 h and then concentrated to dryness. The brownish residue which remains is taken up in 100 ml of methylene chloride˙and extracted three times with 50 ml of water each time. After the organic phase has been dried over sodium sulfate, the brownish clear solution is substantially concentrated and the oil residue is chromatographed over a 2×30 cm silica gel column with methylene chloride/ethanol (98+2) as the eluting agent. After the chromatographically uniform product fraction has been concentrated, the yellowish residue which remains is taken up in 5 ml of methylene chloride, and ethereal hydrochloric acid is added to the solution. After renewed concentration of the hydrochloride solution to dryness, the residue in the form of a solid foam is dissolved in 3 ml of methylene chloride and the product is precipitated as an amorphous substance by dropwise addition of the solution to 1 l of petroleum ether/diethyl ether (2+1). After the precipitate has been filtered off with suction and dried, the title compound is obtained as a fine gray powder of m.p. 118°-128° C. (slow deliquescence); $[\alpha]_D^{22} = +0.9°$ (c=1, methanol); yield: 490 mg.

Starting Compound (−)-3-Methyl-5-(3-bromopropyl)-1,4-dihydro-2,6-dimethyl-4-(3-nitrophenyl)-pyridine-3,5-dicarboxylate 168.5 g of (+)-1-ethoxymethyl-1,4-dihydro-5-methoxycarbonyl-2,6-dimethyl-4-(3-nitrophenyl)-pyridine-3-carboxylic acid/cinchonine salt $\{[\alpha]_D^{22} = +101.5° (c=1, \text{chloroform})\}$ are dissolved in 1.5 l of dichloromethane; 1.2 l of 0.2N hydrochloric acid solution are added with cooling and vigorous stirring. The pH is adjusted to 2 by adding 2N hydrochloric acid solution, and the phases are then separated. The organic phase is washed a total of four times with pH 2 hydrochloric acid solution, and then washed with water, dried over sodium sulfate and concentrated. The obtained oily residue is dissolved in 1.1 l of acetone. 375 g of finely powdered potassium carbonate, 375 ml of 1,3-dibromopropane and 1.2 g of ]18[-crown-6 are subsequently added. The mixture is stirred vigorously for 24 h at room temperature and then filtered by suction; the filter cake is washed with acetone. The filtrate is concentrated under a slight vacuum in a rotary evaporator, and the excess 1,3-dibromopropane is removed by distillation at 0.02 mbar (bath temperature up to 45° C.). 690 ml of concentrated formic acid are poured onto the oily residue with ice cooling; the mixture is then stirred at room temperature unti 1 a cl ear solution has been produced (about 15 minutes). The formic acid is removed by distillation in vacuo. After twice adding and removing (by distillation) 200 ml of toluene in each case, the residue is dissolved in 900 ml of dichloromethane. The solution is stirred with sodium hydrogen carbonate solution (pH 8.5) and washed with water. The organic phase is dried over sodium sulfate and concentrated in vacuo. The product which crystallizes spontaneously after addition of diisopropyl ether is filtered off by suction, washed with diisopropyl ether and dried in vacuo. 102 g of the title compound $\{\text{m.p. } 112° \text{ to } 114° \text{ C.}$ and $[\alpha]_D^{22} = -13.8° (c=1, \text{methanol})\}$ are obtained.

Commercial Applicability

The compounds I and their salts possess valuable properties which make them commercially useful. They are, in particular, antineoplastic agents with an interesting cytostatic activity. They are useful for the treatment of tumors, i.e. for reducing and preventing metastasis and neoplastic growth, in mammals.

In their excellent effectiveness, which is revealed by a selective, controlled i nhi bition of the prol i feration and which is combi ned with 1 ow toxi city and the absence of undesired side-effects, the compounds I and their salts differ in a surprising and advantageous manner from those 1,4-dihydropyridines, the use of which is proposed for cancer chemotherapy in the art. It has to be pointed out, particularly, that up to now only those 1,4-dihydropyridines with pronounced calcium channel blocking (calcium antagonist) activity were regarded as being suitable for cancer chemotherapy, i.e. the calcium channel blocking activity was regarded as a prerequisite for cytostatic activity. It has now been found, surprisingly, that compounds I and their salts, which show only minor calcium channel blocking activity, have a pronounced ability to inhibit tumor cell growth in vitro, which indicates a corresponding in vivo activity.

The minor calcium channel blocking activity of compounds I is revealed by the comparatively small influence of these compounds on the cardiovascular system, e.g. on blood pressure or on heart rate. This low cardiovascular activity of compounds I and their salts permits them to be used in human medicine as potent antitumor and antimetastatic agents: Compounds I and their salts—in contrast to the cardiovascular active calcium channel blockers hitherto known as anti-neoplastic agents—can be administered in a therapeutically-effective amount without risk of undesired side-effects on the cardiovascular system.

The excellent effectiveness of compounds I and of their salts makes them useful in human medicine as chemotherapeutic agents for the treatment of tumors, e.g. ovarian tumors, testicular tumors, carcinomas of the prostate, carcinomas of the urinary bladder, oesophagal carcinomas and other malignant neoplasias, in particular of colon cancer, breast cancer, bronchial carci nomas and lung carcinomas.

The invention therefore al so relates to a process for treating mammals, in particular humans, suffering from one of the noted conditions or diseases. The process is characterized by administering a therapeutically-effective and phar- macologically-acceptable amount of one or more of the compounds of formula I (and/or of pharmacologically-acceptable salts thereof) to a patient in need of such treatment.

The invention relates additionally to the compounds of formula I and their pharmacologically-acceptable salts for use in the treatment of said diseases.

The invention also embraces the use of the compounds of formula I and their pharmacologically-acceptable salts in the preparation of medicaments which are employed for combating said diseases.

The invention also relates to medicaments containing one or more of the compounds of formula I and/or their pharmacologically-acceptable salts.

The medicaments are prepared by processes which are in themselves known and are familiar to those skilled in the art. The medicaments employed are the pharmacologically-active compounds of formula I and/or their pharmacologically-acceptable salts (=active compounds), either as such or, preferably, in combination with suitable pharmaceutical auxiliaries, in the form of tablets, coated tablets, capsules, suppositories, patches (for transdermal drug administration), emulsions, suspensions, aerosols, sprays, ointments, creams, gels or solutions, the content of active compound being advantageously between 0.1 and 95 per cent by weight.

In accordance with the invention, the active compounds are used in any suitable form, provided that the establ i shment and maintenance of sufficient levels of active compound are ensured. This is achieved, for example, by oral, parenteral or inhalative administration in suitable doses. The pharmaceutical formulation of the active compounds is expediently in the form of unit doses appropriate for the desired administration. A unit dose is, for example, a dragee, a capsule, a suppository or a measured volume of a powder, of a granular material, of a solution, of an emulsion or of a suspension.

"Unit dose" for the purpose of the present invention means a physically discrete unit which contains an individual amount of the active ingredient in combination with a pharmaceutical excipient, the content of active compound in the unit dose corresponding to a fraction or a multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain from about 5 to 2500 mg, and in particular from 15 to 1000 mg, of active compound.

In general, it has proved advantageous in human medicine to administer the active compound or compounds, when these are given parenterally, in a daily dose of from about 0.5 to about 30 mg/kg of body weight, if appropriate in the form ofseveral, preferablyl to 3, individual administrations, to achieve the desired results. Similar dosages are used for oral treatment.

The pharmaceutical formulation is administered, for therapeutic purposes, from 1 to 4 times daily at fixed or varying points in time, for example after each meal and/or in the evening. However, it may be necessary to deviate from the dosages mentioned, and in particular to do so in accordance with the nature, body weight and age of the patient to be treated, the nature andseverity of the disease, the nature of the formulation and of the mode of administration of the medicament, and the time or interval over which administration takes place. Thus, in some cases it may be sufficient to manage with less than the abovementioned amount of active compound, while in other cases the noted amount of active compound must be exceeded.

As is customary in internal tumor therapy, treatment with the medicaments according to the invention is optionally combined with administration of other cytostatic agents, having different action spectra, in order to reduce the risk of side-effects. It may also be appropriate to carry out treatment in accordance with the principle of cyclic cytostatic therapy. In this therapy, each treatment is followed by a recovery phase. The experience that, in most organs, healthy tissue regenerates more rapidly than malignant tissue is utilized therein.

The optimum dosage and mode of administration of the active compounds required in each particular case is easily determined by any expert on the basis of his expert knowledge.

The pharmaceutical formulation as a rule consists of the active compound and non-toxic, pharmaceutically-acceptable medicinal excipients, which are used in an admixture or diluent in solid, semi-solid or liquid form, or as a means of encasing, for example in the form of a capsule, a tablet coating, a sachet or some other container, for the therapeutically-active ingredient. An excipient serves, for example, as a promoter of the absorption of the medicament by the body, as a formulating auxiliary, as a sweetener, as a flavor correctant, as a colorant or as a preservative. The various formulations and dosage forms are prepared conventionally other than with regard to the essential active component.

Examples of oral-dosage forms are tablets, dragees, hard and soft capsules, for example made of gelatin, dispersible powders, granules, aqueous and oily suspensions, emulsions, solutions or syrups.

Tablets optionally contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are optionally additionally provided with a coating, which can also be such that delayed dissolution and absorption of the medicament in the gastrointestinal tract and hence, for example, better tolerance, a protracted effect or a retarded effect is achieved. Gelatin capsules contain the medicament mixed, e.g. with solid diluent, for example calcium carbonate or kaolin, or an oily diluent, for example olive oil, groundnut oil or paraffin oil.

Aqueous suspensions optionally contain suspending agents, for example sodium carboxymethylcellulose, methylcellulose hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitan fatty acid esters, such as polyoxyethylene sorbitan monooleate, or lecithin; preservatives, for example methyl or propyl hydroxybenzoate flavoring agents; and sweeteners, for example sucrose, lactose, sodium cyclamate, dextrose or invert sugar syrup.

Oily suspensions optionally contain groundnut oil, olive oil, sesame oil, coconut oil or paraffin oil, and thickeners, such as beeswax, hard paraffin or cetyl alcohol; and furthermore sweeteners, flavoring agents and anti oxidants.

Water-dispersible powders and granules optionally contain the active compound mixed with dispersing agents, wetting agents and suspending agents, for example those mentioned previously, as well as with sweeteners, flavoring agents and colorants.

Emulsions contain, for example, olive oil, groundnut oil or paraffin oil, in addition to emulsifying agents, such as gum acacia, gum tragacanth, phosphatides, sorbitan monooleate or polyoxyethylene sorbitan monooleate, and sweeteners and flavoring agents.

For parenteral administration of the medicaments, sterile injectable aqueous suspensions, isotonic salt solutions or other solutions which contain dispering agents or wetting agents and/or pharmacologically-acceptable diluents, for example propylene glycol or butylene glycol, and/or solubilizing agents, for example Tweens ®, Cremophors ® or polyvinylpyrollidone, are used.

Pharmacology

The antineoplastic activity of (—)-3-methyl-5-]3-(4,4-diphenyl-1-piperidinyl)propyl]-1,4-dihydro-2,6-dimethyl-4-(3-nitrophenyl)-pyridine-3,5-dicarboxylate hydrochloride (compound 1) was testedwin a number of different in vitro assay systems. The tests are descri bed in more detai 1 as follows:

1. Dose-response-relationship of the Anticarcinogenic Effect of 1 in the Human Lung Carcinoid Derived Cell Line NCI-H 727

Methods and Results

Cell line NCI-H 727 was seeded at a density of $5 \times 10$ cells/ml in 50 ml tissue culture flasks. The cells were maintained in RPMl 1640 medium supplemented with L-glutamine (2 mM), fetal bovine serum (10 V/V) and gentamycin sulfate (50 μg/ml) at 7% $CO_2$, 93% air. One day after seeding of cells the test compound was added to the tissueculture medium. The medium containing the test compound was removed on day 3 and replaced with fresh tissue culture medium. The results are given in Table 1.

TABLE 1

Dose-response-relationship of the anticarcinogenic effect of 1 in the human lung carcinoid-derived cell line NCI-H 727

| Treatment | Seeding | No. of viable cells × 10⁴/ml | | |
|---|---|---|---|---|
| | | 72 hrs | 144 hrs | 216 hrs |
| control | 5 | 5.7 | 8.9 | 38.3 |
| Polyethylene glycol-control | 5 | 7.5 | 28.7 | 72.8 |
| 1 1.0 μM | 5 | 0 | 0 | 0 |
| 1 0.5 μM | 5 | 1.2 | 1.3 | 1.6 |
| 1 0.1 μM | 5 | 1.7 | 1.9 | 2.8 |

2. Effect of 1 on Growth Kinetics of the Human Lung Adenocarcinoma-derived Cell Line NCI-H 322 (Clara Cell)

Methods and Results

Cell line NCI-H 322 was seeded at a density of $5 \times 10^4$ cells/ml in 50 ml tissue culture flasks. The cells were maintained in RPMI 1640 medium supplemented with L-glutamine (2 mM), fetal bovine serum (10 V/V) and gentamycin sulfate (50 μg/ml) at 7% $CO_2$, 93% air. One day after seeding of cells (to allow for cell attachment) the test compound listed in Table 2 at the specified concentrations was added to the tissue culture flasks. Cells were trypsinized and counted after staining with trypan blue at the time intervals specified in Table 2. It should be noted that with this methodology only viable cells are detectable because the non-viable cells are being washed off (since non-attached) during harvesting. The results are given in Table 2.

TABLE 2

Dose-response-relationship of the anticarcinogenic effect of 1 in the human lung adenocarcinoma-derived cell line NCI-H 322 (Clara cell)

| Treatment | Seeding | No. of viable cells × 10⁴/ml | | |
|---|---|---|---|---|
| | | 72 hrs | 144 hrs | 216 hrs |
| control | 5 | 5.5 | 10.4 | 33.6 |
| Polyethylene glycol-control | 5 | 7.5 | 22.7 | 34.3 |
| 1 1.0 μM | 5 | 0 | 0 | 0 |
| 1 0.5 μM | 5 | 0.7 | 0.9 | 1.9 |
| 1 0.1 μM | 5 | 1.1 | 1.4 | 2.0 |

3. Effect of Ion Growth Kinetics of the Human Lung Adenocarcinoma-derived Cell Line NCI-H 358 (Alveolar Type II Cell)

Methods and Results

Cell line NCI-H 358 was seeded at a density of $5 \times 10$ cells/ml in 50 ml tissue culture flasks. The cells were maintained in RPMI 1640 medium supplemented with L-glutamine (2 mM), fetal bovineserum (10 V/V) and gentamycin sulfate (50 μg/ml) at 7% $CO_2$, 93% air. One day after seeding of cells (to allow for cell attachment) the test compound listed in Table 3 at the specified concentrations was added to the tissue culture flasks. Cells were trypsinized and counted after staining with trypan blue at the time intervals specified in Table 3. It should be noted that with this methodology only viable cells are detectable because the non viable cells are being washed off (since non-attached) during harvesting. The results are gi yen in Table 3.

TABLE 3

Dose-response-relationship of the anticarcinogenic effect of 1 in the human lung adenocarcinoma-derived cell line NCI-H 358 (alveolar type II cell)

| Treatment | Seeding | No. of viable cells × 10⁴/ml | | |
|---|---|---|---|---|
| | | 72 hrs | 144 hrs | 216 hrs |
| control | 5 | 5.8 | 16.8 | 40.6 |
| Polyethylene glycol-control | 5 | 7.6 | 25.9 | 80.6 |
| 1 1.0 μM | 5 | 0 | 0 | 0 |
| 1 0.5 μM | 5 | 0.9 | 1.1 | 1.8 |
| 1 0.1 μM | 5 | 0.9 | 1.2 | 2.0 |

The invention and its advantages are readily understood from the preceding description. Various changes may be made in the products, in the compositions, in the synthesis and in the mode of administration without departing from the spirit and scope of the invention or sacrificing its material advantages. The products, compositions, synthesis and mode of administration hereinbefore described are merely illustrative of preferred embodiments of the invention.

What is claimed is:

1. A method of reducing susceptible metastasis and neoplastic growth in a mammal which comprises administering to the mammal a therapeutically-effective amount of an optically-pure antineoplastic compound having only inferior calcium channel blocking activity and of formula I $$\text{(I)}$$

wherein
Ar is a 3-nitrophenyl or 2,3-dichlorophenyl;
R1 is methyl;
R2 is methyl or amino;
R3 is methyl or ethyl;
each of R6, R7, R8 and R9 is hydrogen;
A is ethylene, propylene or A1-O-A2;
A1 is ethylene; and
A2 is ethylene;
or a pharmacologically-acceptable salt thereof.

2. A method according to claim 1, which comprises administering to the mammal a therapeutically-effective amount of a compound of formula I according to claim 1, wherein Ar is 3-nitrophenyl or 2,3-dichlorophenyl; each of R1 and R2 is methyl; R3 is methyl or ethyl; each of R6, R7, R8 and R9 is hydrogen; and A is ethylene or propylene; or of a pharmacologically-acceptable salt thereof.

3. A method according to claim 1, which comprises administering to the mammal a therapeutically-effective amount of a compound of formula I according to claim 1, wherein Ar is 3-nitrophenyl or 2,3-dichlorophenyl; R1 is methyl; R2 is methyl or ethyl; each of R6, R7, R8 and R9 is hydrogen; and A is ethylene or propylene; or of a pharmacologically-acceptable salt thereof.

4. A method according to claim 1, which comprises administering to the mammal a therapeutically-effective amount of a compound of formula I according to claim 1, wherein Ar is 3-nitrophenyl or 2,3-dichlorophenyl; each of R1 and R2 is methyl; R3 is methyl or ethyl; each of R6, R7, R8 and R9 is hydrogen; and A is A1-0-A2; A1 is ethylene; and A2 is ethylene; or of a pharmacologically-acceptable salt thereof.

5. A method according to claim 1, which comprises administering to the mammal a therapeutically-effective amount of a compound of formula I according to claim 1, which is (R)-(+)-3-methyl-5-[3-(4,4-diphenyl-1-piperidenyl)-propyl]-1,4-dihydro-2,6-dimethyl-4-(3-nitrophenyl)-pyridine-3,5-dicarboxylate, or a pharmacologically-acceptable salt thereof.

6. A medicament composition which is useful for treating susceptible tumor-afflicted mammals, the composition comprising non-toxic, pharmaceutically-acceptable medicinal excipient and an effective amount of an optically-pure antineoplastic compound having only inferior calcium channel blocking activity and of formula I

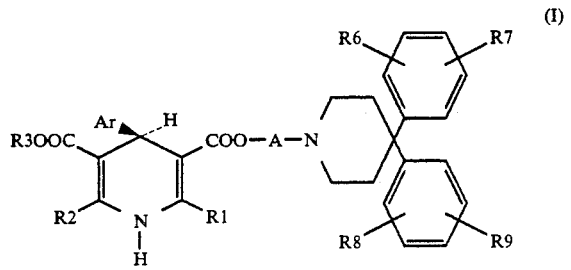

(I)

wherein

Ar is a 3-nitrophenyl or 2,3-dichlorophenyl;
R1 is methyl;
R2 is methyl or amino;
R3 is methyl or ethyl;
each of R6, R7, R8 and R9 is hydrogen;
A is ethylene, propylene or A1-0-A2;
A1 is ethylene; and
A2 is ethylene;
   or a pharmacologically-acceptable salt thereof.

7. A medicament composition of claim 6, wherein the antineoplastic compound is (R)-(+)-3-methyl-5-[3-(4,4-diphenyl-1-piperidinyl)-propyl]-1,4-dihydro-2,6-dimethyl-4-(3-nitrophenyl)-pyridine-3,5-dicarboxylate of a pharmacologically-acceptable salt thereof.

8. A medicament composition according to claim 6, wherein Ar is 3-nitrophenyl or 2,3-dichlorophenyl; each of R1 and R2 is methyl; R3 is methyl or ethyl; each of R6, R7, R8 and R9 is hydrogen; and A is ethylene or propylene; or of a pharmacologically-acceptable salt thereof.

9. A medicament composition according to claim 6, wherein Ar is 3-nitrophenyl or 2,3-dichlorophenyl; R1 is methyl; R2 is amino; R3 is methyl or ethyl; each of R6, R7, R8 and R9 is hydrogen; and A is ethylene or propylene; or of a pharmacologically-acceptable salt thereof.

10. A medicament composition according to claim 6, wherein Ar is 3-nitrophenyl or 2,3-dichlorophenyl; each of R1 and R2 is methyl; R3 is methyl or ethyl; each of R6, R7, R8 and R9 is hydrogen; and A is ethylene or propylene; or of a pharmacologically-acceptable salt thereof.

* * * * *

UNITED STATES PATENT AND TRADEMARK OFFICE
CERTIFICATE OF CORRECTION

PATENT NO. : 5,326,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

Title page, right column, penultimate line, "int eh" should read --in the--. Column 2, line 25, "metastasi s" should read --metastasis--; line 32, "medici ne" should read --medicine--; line 33, "cardi al" should read --cardial--. Column 2, line 34, "alkyl ene" should read --alkylene--; line 37 "and" should start a new line; line 39, "in vitro" should read --*in vitro*--; line 40, "in vivo" should read --*in vivo*--; line 48, "cytostati cactivity" should read --cytostatic activity--. Column 4, line 5, "i ndustri al" should read --industrial--; line 11, "sul" should read --sul- --; line 12, "fosal i cylate" should read --fosalicylate--, "l aurate" should read --laurate--; line 31, "AI-O-A2" should read --A1-O-A2--; line 33, "singl ed" should read --singled--; line 60, "AI-O-A2" should read --A1-O-A2--. Column 5, line 16 "-ethyl[-" should read -- -ethyl]- --; line 20, "dimethyl" should read --dimethyl- --; line 29, "pipe ridinyl)-p ro-" should read --piperidinyl)-pro- --; line 30, "pyl[" should read --pyl]--; line 31, "fluoroethoxi" should read --fluoroethoxy--; line 32 "ethyl[" should read --ethyl]--; line 42, "1,4-2,6" should read --1,4-dihydro-2,6--; line 53, "propyl[" should read --propyl]--; line 54, "4-]3" should read --4-[3--; line 55, "thoxi" should read --thoxy--; line 57, "2,6-4" should read --2,6-dimethyl-4--; line 59, "4,4-...phenyl" should read --4,4-diphenyl--; line 61, "dimethyl pyridine" should read --dimethylpyridine--. Column 6, line 2, "trifluoromethyl phe-" should read --trifluoromethylphe- --; line 5, "dimethyl pyridine-" should read --dimethylpyridine- --; line 8, "dimethyl pyri-" should read --dimethylpyri- --; line 11, "2,6dimethyl" should read --2,6-dimethyl--; line 16, "metho xyethyl" should read --methoxyethyl--; line 26, "ethyl[" should read --ethyl]--; line 27 "6ethyl"

UNITED STATES PATENT AND TRADEMARK OFFICE
CERTIFICATE OF CORRECTION

PATENT NO. : 5,326,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

should read --6-ethyl--; line 38 "d  i" should read --di--; line 42, "trifluoromethyl" should read --trifluoromethyl- --; line 44, "ethyl[" should read --ethyl]--; line 45, "4-]3" should read --4-[3--; line 46, "phenyl[" should read --phenyl]--; line 47, "ethyl[" should read --ethyl]--; line 50, "butyl[" should read --butyl]--; line 57, "6-methyl" should read --6-methyl- --; line 60, "5-]2" should read --5-[2--, "ethyl[" should read --ethyl]--; line 61, "benzox-diazol" should read --benzoxdiazol--; line 62, "methyl pyridine" should read --methylpyridine--; line 63, "5-]2" should read --5-[2--; line 66, "ethyl[" should read --ethyl]--.
Column 7, line 1, "ethyl[" should read --ethyl]--; line 5, "thi enyl" should read --thienyl--; line 9, "nitro phenyl" should read --nitrophenyl--; line 10, "propyl[" should read --propyl]--; line 13, "propyl[" should read --propyl]--; line 23, "propyl[" should read --propyl]--; line 26, "-piperidinyl[" should read -- -piperidinyl]--; line 28, "propyl[" should read --propyl]--; line 29, "trifluoromethyl" should read  --trifluoromethyl- --; line 31, "propyl[" should read --propyl]--; line 32, "6methyl" should read --6-methyl--; line 33, "phenyl[" should read --phenyl]--; line 44, "benxoxazol" should read --benzoxdiazol--; line 46, "S" should read --5--; line 50, "S" should read --5--, "propyl[" should read --propyl]--; line 51, "6methyl" should read --6-methyl--; line 53, "propyl[" should read --propyl]--; line 54, "6methyl" should read --6-methyl--; line 59, "3-]3" should read --3-[3--; line 60, "propoxi" should read --propoxy--; line 63, "pip eri dinyl" should read --piperidinyl--; line 64, "ethoxi" should read --ethoxy--; line 66, "pip eri dinyl" should read

UNITED STATES PATENT AND TRADEMARK OFFICE
CERTIFICATE OF CORRECTION

PATENT NO. : 5,326,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

--piperidinyl--; line 67, "ethoxi" should read --ethoxy--. Column 8, line 8, "ethyl}1,4" should read --ethyl}-1,4--; line 10, "4 4-diphenyl1" should read --4,4-diphenyl-1--; line 12, "fluoromethyl phenyl" should read --fluoromethylphenyl--; line 13, "pip eri dinyl" should read --piperidinyl--; line 14, "4-]3" should read --4-[3--; line 15, "tetrafluoroet ... phenyl[" should read --tetrafluoroethoxy)-phenyl]--; line 27, "benzoxadiazol" should read --benzoxdiazol--; line 29, "p pe r dinyl" should read --piperidinyl--; line 30, "2 6" should read --2,6--; line 35, "2-]2" should read --2-[2--, "p perdinyl" should read --piperidinyl--; line 38, "p pemdinyl" should read --piperidinyl--; line 40 "thi enyl" should read --thienyl--; line 45, "1,4dihydro" should read --1,4-dihydro--; line 59, "fluoromethyl phenyl" should read --fluoromethylphenyl--; line 61, "4-]3" should read --4-[3--; line 62, "phenyl[" should read --phenyl]--. Column 9, lines 3 to 5, delete entire text; line 9, "3-]3" should read --3-[3--; line 12, "piperidyinyl" should read --piperidinyl--; immediately below line 14, insert --(R)-3-methyl-5-{3-[3-(4,4-diphenyl-1-piperidinyl)-propoxy]-propyl}-1,4-dihydro-2,6-dimethyl-4-(2-methoxyphenyl)-pyidine-3,5-dicarboxylate--. Column 10, line 13, "sul foxi de" should read --sulfoxide--; line 45, "obtai ned" should read --obtained--; line 67, "Z-A-Z" should read --Z-A-Z--. Column 11, line 52, "exemplaryselection" should read --exemplary selection--. Column 12, line 65, "exemplaryselection" should read --exemplary selection--. Column 13, line 21, "withsecondary" should read

UNITED STATES PATENT AND TRADEMARK OFFICE
CERTIFICATE OF CORRECTION

PATENT NO. : 5,327,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

--with secondary--. Column 14, line 10, "propyl[" should read --propyl]--; line 17, "suitableseparation" should read --suitable separation--; line 44, "acid-additi on" should read --acid-addition--; line 61, "(-)-3-Methyl" should read --1. (-)-3-Methyl--. Column 15, line 21, "[α]...=-39°" should read --$[\alpha]_{436}^{22}=-39°$--; line 22, "[α]=-14,4" should read --$[\alpha]_D^{22}=-14.4$--; line 29, "sol" should read --sol- --; line 35, "[α]...or" should read --$[\alpha]_D^{22}$ or--; line 36, "boi l" should read --boil--; line 45, "obtainedsecond" should read --obtained second--; line 47, "[α]...=" should read --$[\alpha]_D^{22}$ line 48, "[α]...=" should read --$[\alpha]_D^{22}=$--; line 56, "[α]...=" should read --$[\alpha]_D^{22}=$--; line 58, "5-]3" should read --5-[3--; line 59 "propyl[" should read --propyl]--; line 64, "di0,0'" should read --di-0,0'--; line 65, "[α]...=" should read --$[\alpha]_D^{22}=$--. Column 16, line 4, "[α]...=" should read --$[\alpha]_D^{22}=$--; line 7, "crops" should read --crop--; lines 9 and 10, "wi th" should read --with--; line 21, "[α]...=" should read --$[\alpha]_D^{22}=$--; line 27, "[α]...=" should read --$[\alpha]_D^{22}=$--; line 29, "(+)-3-Methyl" should read --3. (+)-3-Methyl--, "piperidinyl" should read --piperidinyl)--; line 42, "ethyl[" should read --ethyl]--; line 47, "chloride'" should read --chloride --; line 67, "[α]...=" should read --$[\alpha]_D^{22}=$--. Column 17, line 9, "[α]...=" should read --$[\alpha]_D^{22}=$--; line 13, "thenseparated" should read --then separated--; line 17, "1.11" should read --1.1 l--; line 19, "]18[" should read --[18]--; line 28, "unti l a cl ear" should read --until a clear--; line 40, "[α]...=" should read --$[\alpha]_D^{22}=$--; line 50, "aselective" should read --a selective--, "i nhi bition" should read --inhibition --, "prol i feration"

UNITED STATES PATENT AND TRADEMARK OFFICE
CERTIFICATE OF CORRECTION

PATENT NO. : 5,326,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

should read --proliferation--; line 51, "combi ... city" should read --combined with low toxicity--; line 64, "in vitro" should read --*in vitro*--; line 65, "in vivo" should read --*in vivo*--. Column 18, line 17, "carci nomas" should read --carcinomas--; line 18, "al so" should read --also--; line 22, "phar- macologically" should read --pharmacologically--; line 51, "establ i shment" should read --establishment--; line 62, "activeingredient" should read --active ingredient--. Column 19, line 15, "ofseveral, preferablyl" should read --of several, preferably 1--; line 24, "andsever-" should read --and sever- --; line 29, "abovementioned" should read --above-mentioned--. Column 20, line 7, "e.g." should read --e.g.,--; line 12,"methylcellulose" should read --methylcellulose,--; line 19, "droxybenzoate" should read --droxybenzoate;--; line 26, "anti oxidants" should read --antioxidants--; line 47, "5-]" should read --5-[--; line 48, ")propyl" should read --)-propyl--; line 50, "testedwin" should read --tested in--; line 51, "in vitro" should read --*in vitro*--, "descri bed" should read --described--; line 52, "detai 1" should read --detail--; line 59, "10" should read --$10^4$--; line 65, "tissueculture" should read --tissue culture--. Column 21, line 49, "Ion" should read --1 on--; line 54, "10" should read --$10^4$--; line 57, "bovineserum" should read --bovine serum--; line 68, "g yen" should read --given--. Column 22, line 44, "Ar is a" should read --Ar is--; line 66, "R2" should read --R2 is amino; R3--. Column 23, line 14, "piperidenyl" should read --piperidinyl--. Column 24, line 1, "Ar is a" should read --Ar is--;

UNITED STATES PATENT AND TRADEMARK OFFICE
CERTIFICATE OF CORRECTION

PATENT NO. : 5,326,772

DATED : July 5, 1994

INVENTOR(S) : Kurt KLEMM, Wolf-Rudiger ULRICH, Dieter FLOCKERZI

It is certified that error appears in the above-identified patent and that said Letters Patent is hereby corrected as shown below:

```
line 15, "of" should read --or--; lines 31 and 32, "is
ethylene or propylene" should read --is A1-O-A2; A1 is
ethylene; and A2 is ethylene--.
```

Signed and Sealed this

Tenth Day of January, 1995

*Attest:*

BRUCE LEHMAN

*Attesting Officer*     Commissioner of Patents and Trademarks